United States Patent [19]

Bononi

[11] Patent Number: 4,472,402

[45] Date of Patent: Sep. 18, 1984

[54] AMINO ALKYLSULPHONIC DERIVATIVES, A PROCESS FOR THEIR PREPARATION AND PHARMACEUTICAL COMPOSITIONS CONTAINING SAID DERIVATIVES

[76] Inventor: Loris J. Bononi, Castiglione del Terziere, Gabbiana (Massa Carrara), Italy

[21] Appl. No.: 568,314

[22] Filed: Jan. 4, 1984

[30] Foreign Application Priority Data

Jan. 7, 1983 [IT] Italy ............................. 19027 A/83

[51] Int. Cl.³ .................. A61K 31/505; C07D 239/02
[52] U.S. Cl. .................................... 424/251; 544/327
[58] Field of Search ....................... 544/327; 424/251

[56] References Cited
PUBLICATIONS

Chem. Abst., vol. 82, 1975, p. 548, 155643d.

Ibrahim Zeid et al., Liebigs Ann. Chem., 1974, pp. 1816-1819.

Primary Examiner—Donald G. Daus
Assistant Examiner—Cecilia Shen
Attorney, Agent, or Firm—Pollock, Vande Sande & Priddy

[57] ABSTRACT

The compounds having the formula:

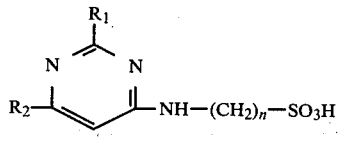

wherein $R_1$ and $R_2$ represent halogen atoms and $n=3$ or 4, are endowed with anti-viral activity, particularly in the treatment of herpetic keratitis and of *Herpes genitalis.*

4 Claims, No Drawings

AMINO ALKYLSULPHONIC DERIVATIVES, A PROCESS FOR THEIR PREPARATION AND PHARMACEUTICAL COMPOSITIONS CONTAINING SAID DERIVATIVES

Amino alkylsulphonic derivatives, a process for their preparation and pharmaceutical compositions containing said derivatives.

The present invention relates to N-substituted aminoalkylsulphonic derivatives having antiviral activity. More specifically the present invention relates to the compounds having the following formula:

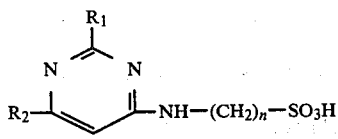

wherein $R_1$ and $R_2$, identical to or different from each other, represent a halogen atom and $n=3$ or 4.

The compounds of the present invention are antiviral agents active against the following viruses: Herpes Simplex Virus, Polio Virus, Vaccinia Virus. As regards the Herpes Simplex Virus, the compounds of the present invention permit the treatment of the following infections induced by these viruses: herpetic keratitis and Herpes genitalis. The herpetic keratitis is considered as the most frequent cause of sight loss originated by an external infection of the eye. The Herpes Genitalis is a venereal diseases of relevant, social and nosological, importance, which may be associated to gonorrhea and trichomoniasis as well as to other infections. The lesions affect, in the women, the vagina, the vulva, the cervix and the perineum, and in the man the glans, the prepuce. There is a suspect also that Herpes Genitalis is a cancer cause in the woman.

It is known that 2-amino-4,6-dichloropyrimidine prevents from being formed the capsidic proteins, capable of organizing with the viral RNA complete and infecting particles of poliovirus (Experientia 29/II, 1442-43, 15-II-1973), and that such an effect is irreversible since the substance is readily accepted and retained by the infected cells (Experientia 29/12, 1559-61, 15-II-1973).

It is also known that 2-amino-4,6-dichloropyrimidine is capable of inhibiting the reproduction of Herpes Simplex Virus in a complete culture medium and in the presence of mercaptoethanolamine (Experientia, 30/II, 1272-73, 15-II-1974) and that the treatment of herpetic keratitis in the rabbit carried out with the two aforesaid substanced is efficacious (Annales New York Acad. of Sciences, Vol. 284, 294-304,4-3-1977). The action of 2-amino-4,6-dichloropyrimidine, lastly, is a specific one, permitting, at definitely antiviral doses and combinations, a normal synthesis of nucleic acids and proteins in non infected cells, and their normal entrance in the mitosis (G. Ital.Chemiot. 21, 95-108, 1974).

U.S. Pat. No. 3,991,190 does furthermore teach the treatment of viral infections induced by Herpes Simplex and by poliovirus. To this end the aforesaid U.S. patent suggests a composition comprising a pyrimidine compound, such as the above mentioned one, namely 2-amino-4,6-dichloropyrimidine, and the acetamido and formamido derivatives, preferably in combination with cysteamine.

The main object of the present invention are the novel compounds of formula (I) which are active as anti-viral agents in the treatment of herpetic keratitis and of Herpes Genitalis. Among the compounds of the present invention the 3-(2,6-dichloro-4-pyrimidylamino)-propan-1-sulphonic acid, is preferred, having the formula:

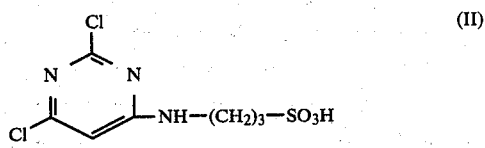

The present invention also contemplates the process for the preparation of the compounds of formula (I), this process comprising the steps of reacting the suitable starting pyrimidine with an alkylsulphone by heating in a solvent such as asbsolute ethanol, according to the general method disclosed for the preparation of aminoalkylsulphonic acids derived from pyrimidines by I. Zeid., H. Moussa and I. Ismail, Liebigs Ann. Chem. (1974), 1816. Aminopyrimidines readily react in boiling ethanol with propane sultone or butansultone

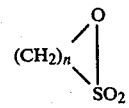

to give the respective alkylsulphonic derivatives.

The synthesis of the starting pyrimidine is preferably carried out according to the method described by Rupe et al, (Helv. Chim. Acta, 8, 848, 1925), and by Bergman and Johnson (J. Am. Chem. Soc. 55, 1733, 1933) with a subsequent chlorination with phosphorous oxychloride according to the method of Langerman (J. Am. Chem. Soc., 73, 3011, 1951).

In the following example there is illustrated the preparation of the preferred compound of the present invention, namely the 3-(2,6-dichloro-4,-pyrimidylamino)-propan-1-sulphonic acid.

1.54 g of 4-amino-2,6-dichloropyrimidine (0.01 moles) and 1.22 g of 1.3-propansulphone (0.01 moles) are boiled to reflux for 6 hours in absolute ethanol. During the reaction a precipitate is formed. At the end of the 6 hour time the reaction mixture is cooled and filtered. The compounds (II) is obtained with a practically quantitative yield. The IR and NMR spectra confirm that the compound has the foreseen structure. With this compound compositions useful for topical use were prepared.

More specifically an eye wash composition was prepared having the following recipe:
 compound (II): 0.4 g
 sodium carboxymethylcellulose: 0.5 g
 propylene glycol: 28.0 g
 distilled water: enough to 100 ml This collyrium was daily administered, in the amount of 2 drops per eye, to patients suffering from herpetic keratitis until the disease was resolved. With this compound (II) a colloidal gel was also prepared and topically daily applied to patients suffering from Herpes Genitalis. In this case too the lesions disappeared after some treatment days.

Generally, for the therapeutical use of the compounds of the invention all the forms of pharmacologically acceptable ointments, creams and lotions are foreseen, the recipe of which comes within the scope of the normal pharmaceutical techniques both as regards the ingredients (vehicles, excipients), and as regards the preparation. Although the mechanism of action of the compounds of the invention has not yet been fully clarified, it seems reasonable to attribute to the alkylsulphonic substituent the property of promoting the penetration of the active principle (namely the dichloropyrimidine nucleous) into the skin and the mucosae, namely into the reproduction sites of the virus. At the same time the compounds of the invention render it no longer determining the presence of co-agents for attaining the anti-viral activity.

I claim:

1. Aminoalkylsulphonic compounds, having the formula:

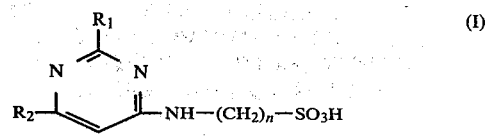

wherein $R_1$ and $R_2$, identical to or different from each other, represent a halogen atom and $n=3$ or 4.

2. 3-(2,6-dichloro-4-pyrimidylamino)-propan-1-sulphonic acid.

3. Pharmaceutical composition having anti-viral activity for topical use, characterized by containing a compound according to claim 1 in combination with the normal vehicles and excipients for topical preparations.

4. Pharmaceutical composition useful for the treatment of herpetic disease having anti-viral activity for topical use, characterized by containing a compound according to claim 2 in combination with the normal vehicles and excipients for topical preparations.

* * * * *